(12) United States Patent
Measamer (10) Patent No.: US 8,052,698 B2
(45) Date of Patent: Nov. 8, 2011

(54) SURGICAL INSTRUMENT

(75) Inventor: John P. Measamer, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 998 days.

(21) Appl. No.: 11/755,518

(22) Filed: May 30, 2007

(65) Prior Publication Data
US 2008/0300608 A1 Dec. 4, 2008

(51) Int. Cl.
*A61B 17/08* (2006.01)

(52) U.S. Cl. ........................ 606/153; 606/220

(58) Field of Classification Search .............. 606/139, 606/142, 153, 219; 600/104
See application file for complete search history.

(56) References Cited

U.S. PATENT DOCUMENTS

| | | | |
|---|---|---|---|
| 6,086,600 A * | 7/2000 | Kortenbach | 606/139 |
| 6,916,332 B2 * | 7/2005 | Adams | 606/219 |
| 6,966,919 B2 | 11/2005 | Sixto et al. | |
| 7,033,378 B2 | 4/2006 | Smith et al. | |

* cited by examiner

*Primary Examiner* — Julian Woo
(74) *Attorney, Agent, or Firm* — Welsh Flaxman & Gitler LLC (57) ABSTRACT

A surgical instrument for applying a fastener to tissue. The instrument includes a shaft having a working end and a grip end, a first jaw pivotally mounted on the working end including a receiver for releasably holding a male component and a second jaw statically mounted on the working end including a receiver for releasably holding a female component. The first jaw is pivotally moveable between an open position in which the first jaw is sufficiently spaced from the second jaw so tissue can be received between a male component and a female component, and a closed position in which a protrusion of the male component is aligned with and received in a recess of the female component. The instrument includes a mechanism operatively connected to the first jaw for moving the first jaw between the open position and the closed position.

9 Claims, 9 Drawing Sheets

SURGICAL INSTRUMENT

BACKGROUND

This invention generally relates to a surgical instrument, and more particularly to an instrument for applying a fastener to tissue of a patient.

Gastroesophageal reflux disease or persistent heartburn is caused by an improper relaxation of the lower esophageal sphincter, allowing acidic stomach contents to travel into the esophagus. If left untreated, chronic reflux may cause esophageal stricture, bleeding ulcers, perforation, and scarring. Continued reflux may lead to Barrett's esophagus, involving changes in the esophageal cells and possibly leading to cancer. Antacids and proton pump inhibitors are initially used to treat this condition. If these treatments are unsuccessful, surgical intervention is often recommended.

One interventional surgical method is known as Nissen fundoplication. This procedure involves wrapping a fundus of the stomach around the lower end of the esophagus and fastening it in place to make the lower esophageal sphincter less compliant. Traditionally, this procedure was accomplished by open surgery using sutures to secure the plicated fundus of the stomach around the esophagus without penetrating the stomach. More recently, laparoscopic Nissen procedures have been used. In some laparoscopic procedures, surgical fasteners are used with an endoscopic applicator. Several different fastener designs have been developed. Some of these designs include a two piece fastener. A first of these pieces, a male component, includes a base having two straight elongate needles extending perpendicularly outward from the base generally parallel to each other. A second piece, a female component, includes a receiver element having openings positioned for receiving the needles of the first piece and a lock for holding the needles in place once received in the openings. In use, tissue is gathered, the needles of the first piece are pushed through the gathered tissue and the openings of the second piece to hold the tissue and fastener in place.

Various applicators are used to apply the fastener to the tissue. One applicator includes an elongate shaft having two jaws pivotally attached to its end. The jaws include receptacles for holding the first and second pieces of the fastener. The jaws push the needles of the first piece through the gathered tissue and the openings of the second piece to hold the tissue and fastener in place. As will be appreciated by those skilled in the art, because both jaws are pivotally attached to the shaft, both pieces of the fastener sweep through arcs as the jaws pivot to pierce the tissue and push the needles into the corresponding openings. As a result of the fastener pieces sweeping through arcs, both fastener pieces move relative to the tissue, making precise placement of the fastener in the tissue difficult. Even when the needles engage the tissue, the folded tissue can move relative to the female fastener component before the fastener components are fastened together. Thus, there is a need for an applicator that reduces the opportunity for the tissue to move as the fastener is applied.

BRIEF SUMMARY

The present invention relates to a surgical instrument for applying a fastener to tissue of a patient. The fastener comprises a male component including a base and a protrusion, and a female component including a base and a recess for receiving the protrusion of the male component. The instrument comprises an elongate shaft having a working end and a grip end opposite the working end. Further, the instrument includes a first jaw pivotally mounted on the working end of the elongate shaft including a receiver for releasably holding the base of the male component. In addition, the instrument includes a second jaw statically mounted on the working end of the elongate shaft including a receiver for releasably holding the base of the female component. The first jaw is pivotally moveable between an open position in which the first jaw is sufficiently spaced from the second jaw so that tissue can be received between a female component held in the first jaw and a male component held in the first jaw of the instrument and a closed position in which the protrusion of the male component is aligned with and received in the recess of the female component. Still further, the instrument includes a mechanism operatively connected to the first jaw for moving the first jaw between the open position and the closed position to join the male component of the fastener with the female component of the fastener thereby applying the fastener to the tissue of the patient.

In another aspect, the present invention relates to a surgical instrument for applying a fastener to tissue of a patient. The fastener comprises a male component including a base and a protrusion, and a female component including a base and a recess for receiving the protrusion of the male component. The instrument comprises an elongate shaft having a working end and a grip end opposite the working end. Further, the instrument includes a stationary jaw statically mounted on the working end of the shaft including a receiver for holding the male component or the female component. In addition, the instrument comprises a pivoting jaw mounted on the working end of the elongate shaft adjacent the stationary jaw. The pivoting jaw includes a receiver for releasably holding the other of the male component and the female component. The pivoting jaw selectively pivots between an open position in which tissue can be received between the jaws and a closed position in which the protrusion of the male component is aligned with and received in the recess of the female component.

Other aspects of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
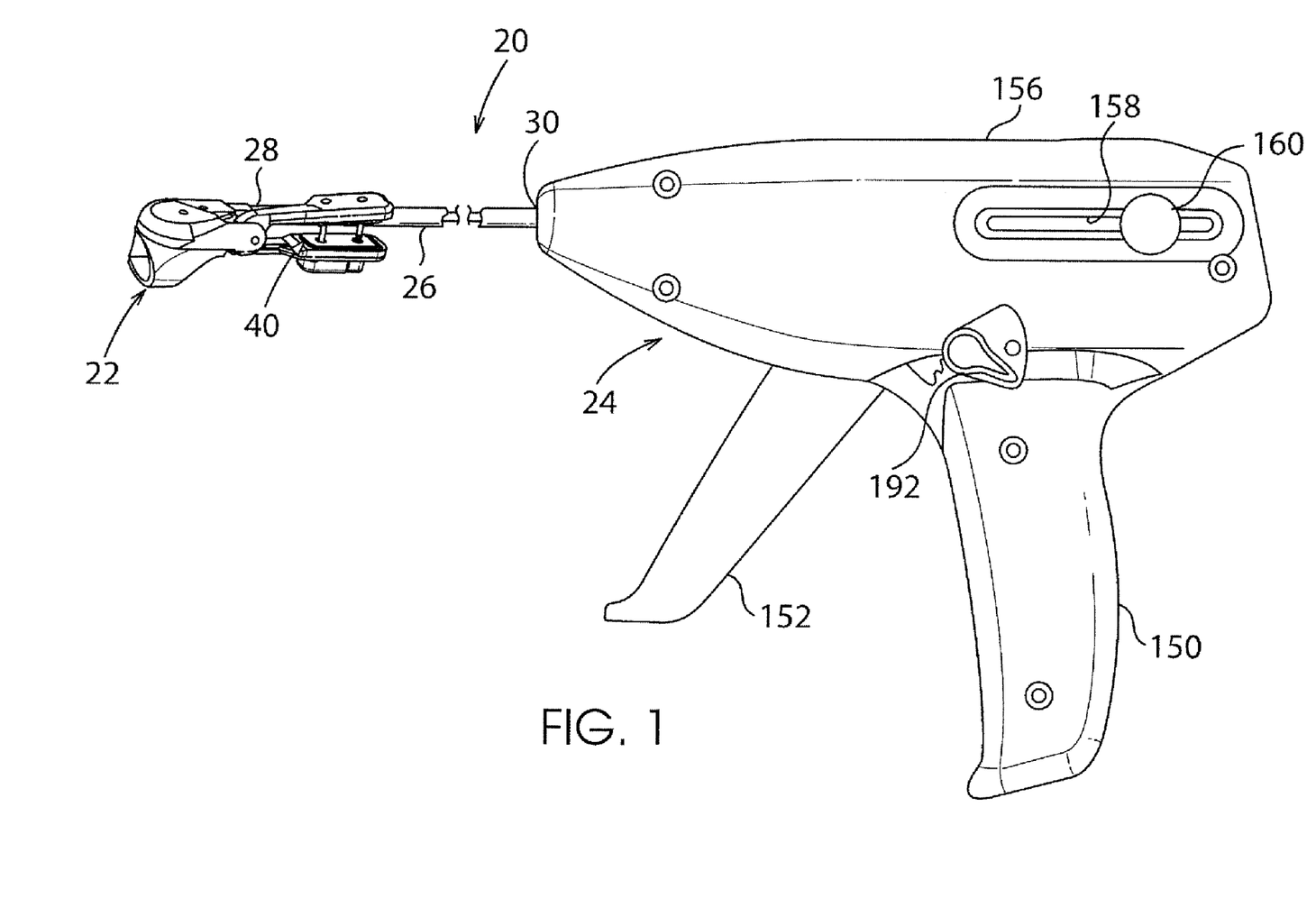
FIG. 1 is a fragmented side elevation of a surgical instrument of the present invention.

Referring now to the drawings and in particular FIG. 1, a surgical instrument of the present invention is generally designated by the reference number 20. The instrument is specifically adapted for performing endoscopic surgery to fold and fasten tissue. The instrument 20 generally includes an end effector (generally designated by 22) and a handle assembly (generally designated by 24) mounted on opposite ends of an elongate shaft 26. The shaft 26 has a working end 28, on which the end effector 22 is mounted, and a grip end 30, on which the handle assembly 24 is mounted.

In one embodiment, the shaft 26 is a flexible hollow tube having a circular cross section, a length of between about fifth centimeters (cm) and about 150 cm, and an outside diameter of between about 2.5 millimeters (mm) and about five mm. Although the shaft 26 may be made of other materials without departing from the scope of the present invention, in one embodiment the shaft is made of coiled stainless steel.

Figure 2:
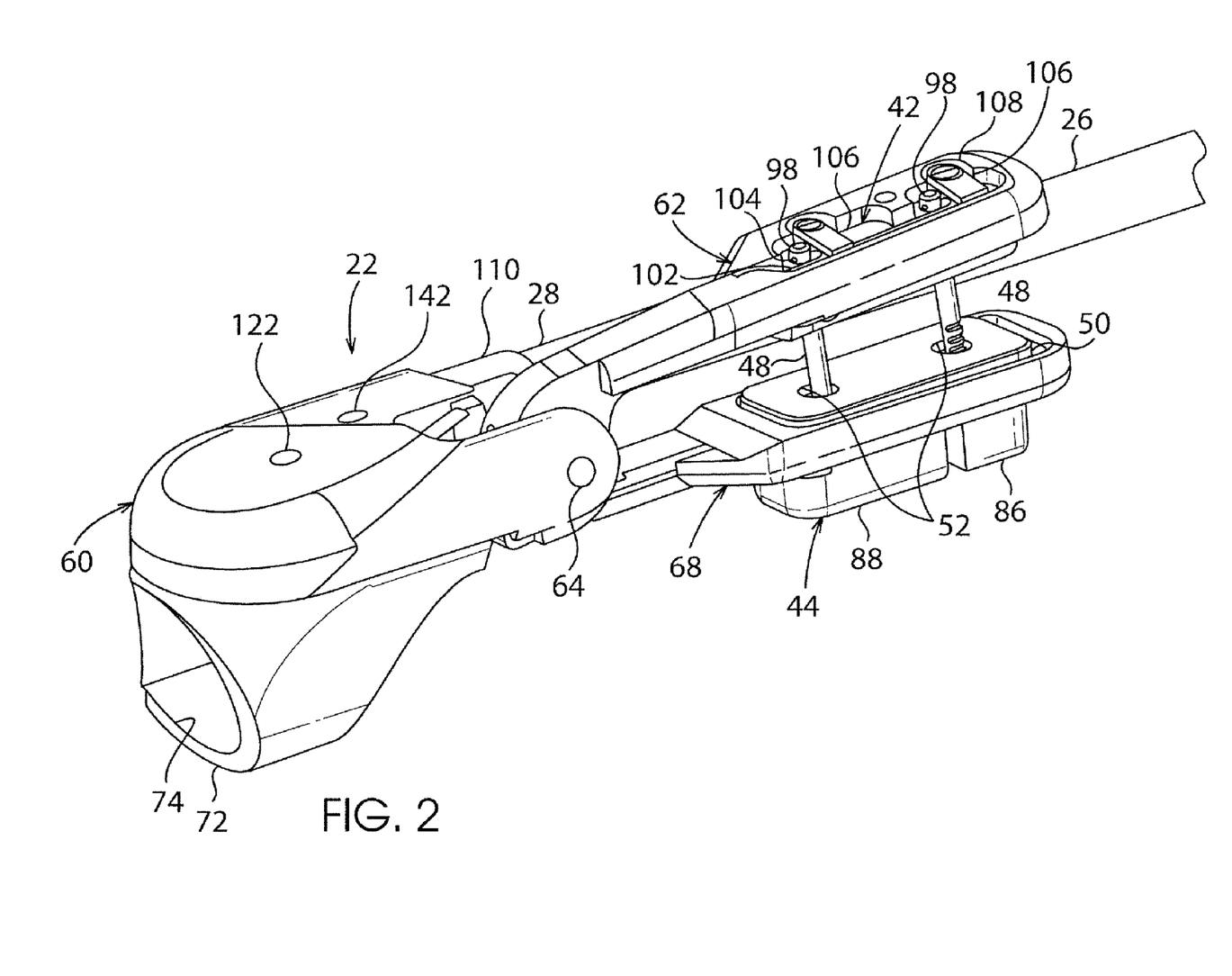
FIG. 2 is a perspective of an end effector of the surgical instrument shown with a fastener while in a closed position.
Figure 3:
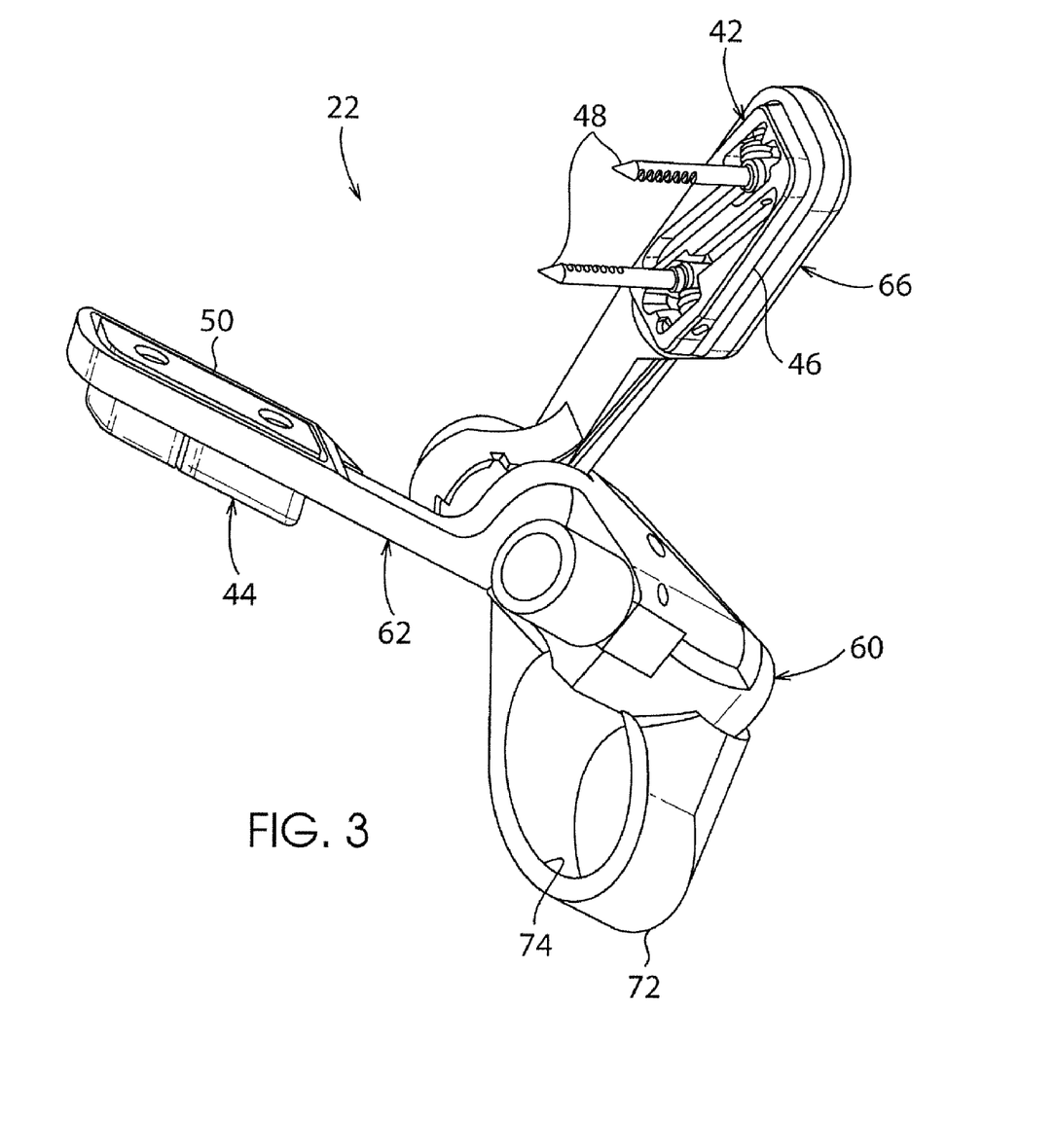
FIG. 3 is a the perspective of the end effector shown with a fastener while in an open position.

The end effector 22 is adapted apply a two-part fastener 40 to tissue to hold it in position. Although the end effector 22 may be adapted to apply other types of fasteners without departing from the scope of the present invention, in one embodiment the end effector is adapted for use with a two-part fastener, generally designated by 40, such as described in U.S. Pat. No. 7,033,378. As shown in FIGS. 2 and 3, the fastener 40 includes a male component, generally designated by 42, and a female component, generally designated by 44. The male component 42 includes a base 46 and needles or protrusions 48 extending outward from the base. The female component 44 includes a base 50 and openings or recesses 52 for receiving the needles 48 of the male component 42. As the use and construction of two-part fasteners 40 such as disclosed in U.S. Pat. No. 7,033,378 are well known by those skilled in the art, they will not be described in further detail. The female component 44 includes a lock 54 for locking the female component on the male component 42 when the protrusions are positioned in the recesses 52.

As shown in FIG. 2, the end effector 22 includes a housing, generally designated by 60, mounted on the working end 28 of the shaft 26. The end effector 22 includes a first jaw or male jaw, generally designated by 62, pivotally mounted on the housing 60 with a pin 64. The male jaw 68 includes a generally rectangular receptacle or receiver 66 (FIG. 4) adapted for receiving a base 46 of a male component 42 as illustrated. The end effector 22 also includes a first jaw or female jaw, generally designated by 68, statically mounted on the housing 60. The female jaw 68 extends generally parallel to the shaft toward the grip end 30 of the shaft 26. The female jaw 68 includes a generally rectangular receptacle or receiver 70 (FIG. 4) adapted for receiving a base 50 of a female component 44 as illustrated in FIG. 2. The receptacle 64 of the male jaw 68 receives the base 46 of the male component 42 as illustrated so the needles 48 of the male component generally face the openings 52 in the female component 44. The instrument 20 may be actuated as explained below so the male jaw 68 pivots about the pin 64 between an open position as shown in FIG. 3 for receiving tissue between the male and female jaws to a closed position as shown in FIG. 2 for joining the male component 42 of the fastener 40 with the female component 44 of the fastener thereby applying the fastener to the tissue of the patient.

Figure 5:
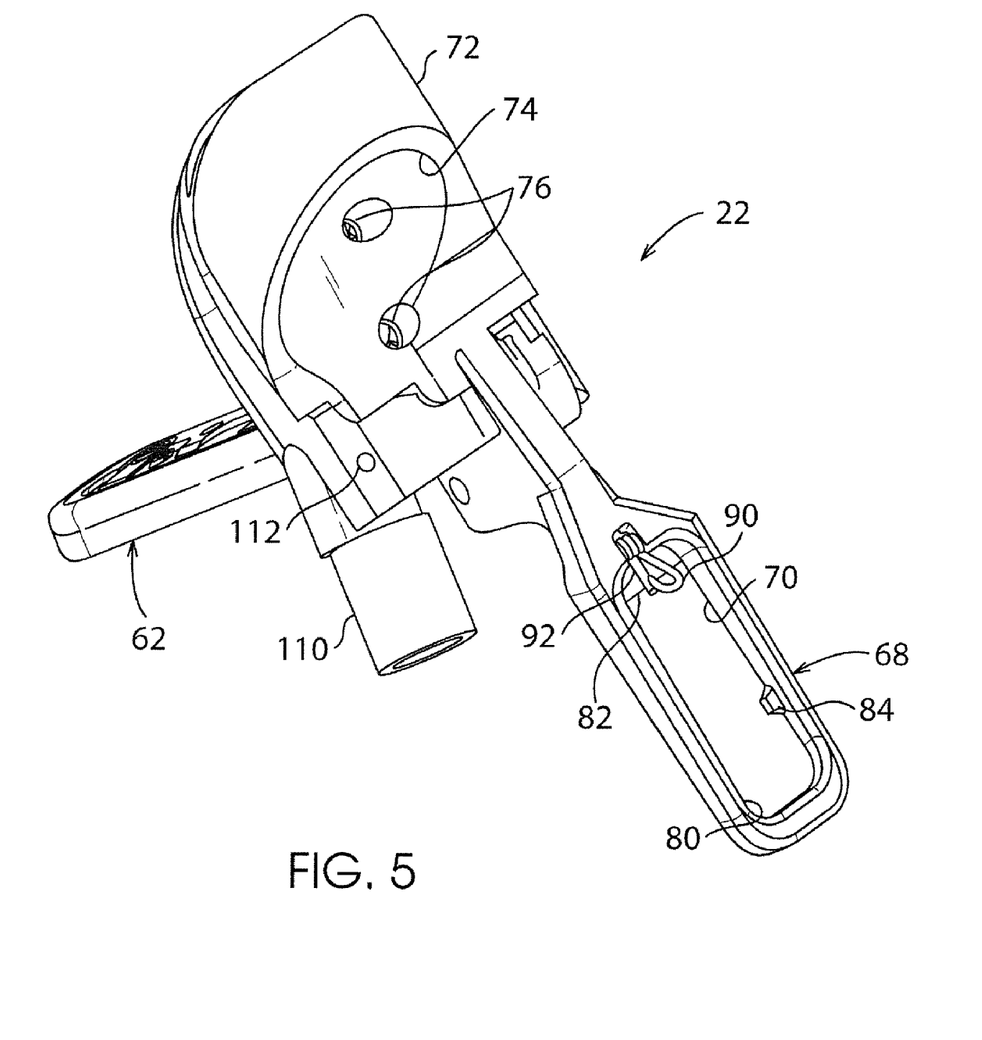
FIG. 5 is a perspective of the end effector shown without the fastener while in the open position.

A sleeve 72 is provided on the housing 60 for receiving a tip of an endoscope (not shown) so the physician can view the tissue as the fastener is applied. The sleeve 72 includes an opening 74 having a diameter corresponding to a small endoscope (e.g., about twelve mm). The sleeve 72 may be mounted on the housing 60 with screw fasteners 76 as shown in FIG. 5 so the sleeve can be removed when not in use to reduce the overall effective cross-sectional area of the instrument 20. Although the sleeve 72 may be made of other materials without departing from the scope of the present invention, in one embodiment the sleeve is made of a soft, low friction, lubricious material such as polytetrafluoroethylene (PTFE), nylon, or silicone to facilitate the endoscope entering the opening 72.

Figure 4:
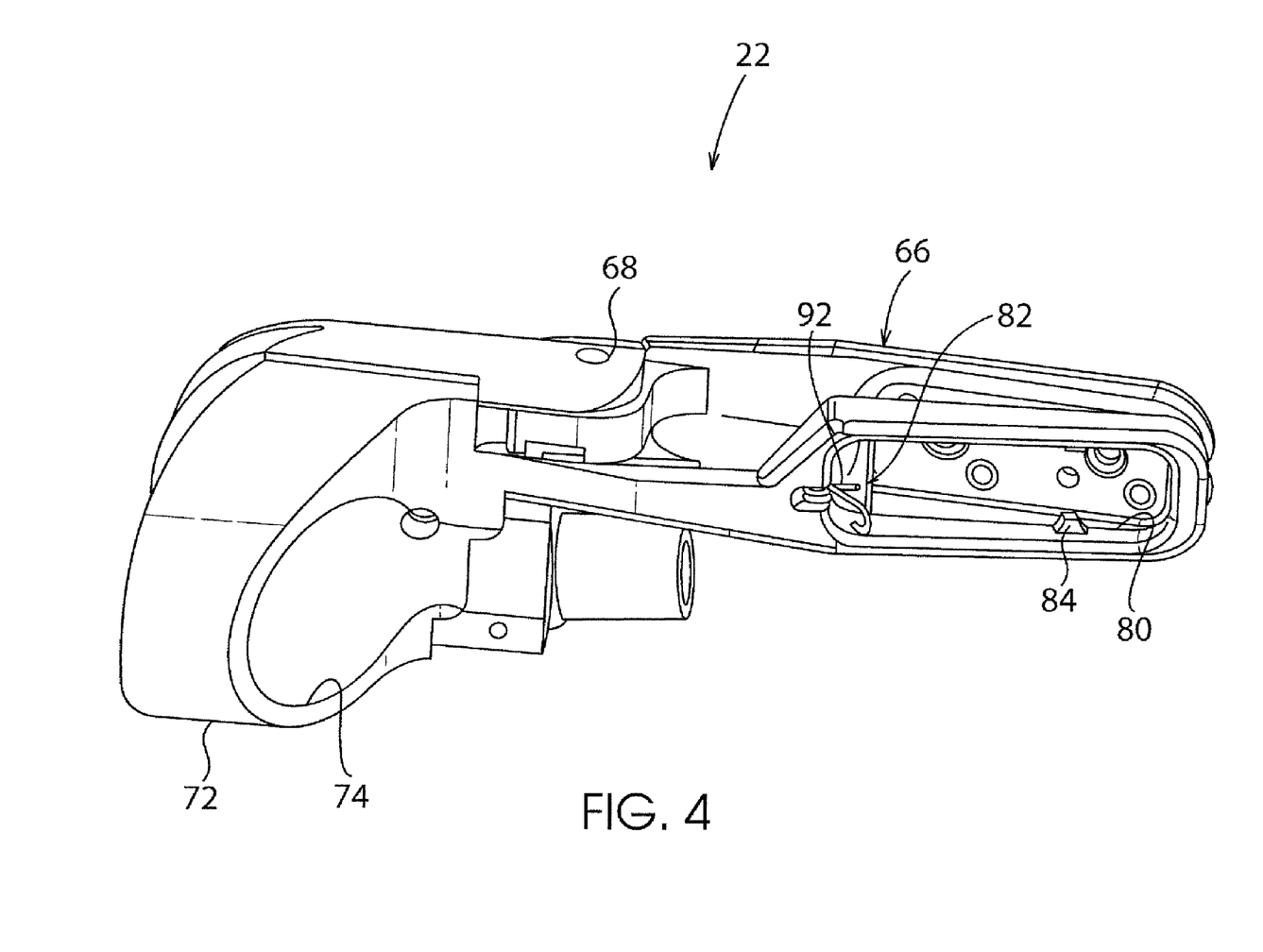
FIG. 4 is a perspective of the end effector shown without the fastener while in the closed position.

As illustrated in FIGS. 4 and 5, the receptacle 70 of the female jaw 68 includes a large rectangular opening 80 that is sized to receive the base 50 of the female component 44 of the fastener 40. The receptacle 64 has a ledge 82 at one end, and a lug 84 extending into the opening 80 from each side. The female component 44 of the fastener 40 is inserted into the opening 80 in a locked position (as shown in FIG. 2) so a locking feature 86 is spaced from a head 88 of the female component. The base 50 of the component 44 is overlapped with the ledge 82 and the locking feature 86 and head 88 are positioned on opposite sides of the lugs 84. Once the female component 44 is in position, the locking feature 86 of the component is moved toward the head 88 so the female component is in an unlocked position (as shown in FIG. 3). When the female component 44 is in the unlocked position, the head 86 overlaps the ledge 82 and the locking feature 86 captures the lugs 84 so the female component 44 is held firmly in the receptacle 70 of the female jaw 68. As shown in FIG. 5, a torsion spring 90 is provided on the female jaw 62 for forcing the female component 44 of the fastener toward the end of the jaw. The torsion spring 90 aligns the female component 44 with the male component 42 as the male jaw 68 is rotated toward the female jaw 68. Further, the female jaw 68 includes a push rod 92 for pushing the female component 46 so it does not overlap the ledge 82 to release the female component from the receptacle 72 as described below.

The male jaw 68 includes a rectangular recess 66 adapted to receive the base 46 of the male component 42 of the fastener 40. The recess 66 includes two counterbored holes 94 and two threaded holes 96. When the male component 42 is loaded into the recess 66 of the male jaw 68, the stub ends 98 of the protrusions 48 are received in the counterbored holes 94 to hold the protrusions in an upright configuration and prevent them from rotating into a collapsed configuration. As shown in FIG. 2, the outside of the male jaw 62 also includes a recess 100. A releasable catch 102 is positioned in the recess 100 for engaging holes 104 provided in each of the stub ends 98 of the protrusions 48 of the male component 42 to hold the component in the receptacle 66. A cantilevered cover 106 is positioned above each threaded hole 96 and held in place with a screw fastener 108. The covers 106 reduce a potential for inadvertently releasing the catch 102 from holes 104 in the stub ends 98 of the protrusions 48 of the male component 42.

Referring to FIG. 5, the housing 60 includes a mount 110 to which the shaft 26 (FIG. 1) is attached. Although the mount 110 may be integrally formed with the housing 60, in one embodiment the mount is pivotally attached to the housing with a pin 112 to permit the end effector 22 angle to be adjusted relative to the shaft 26.

Figure 6:
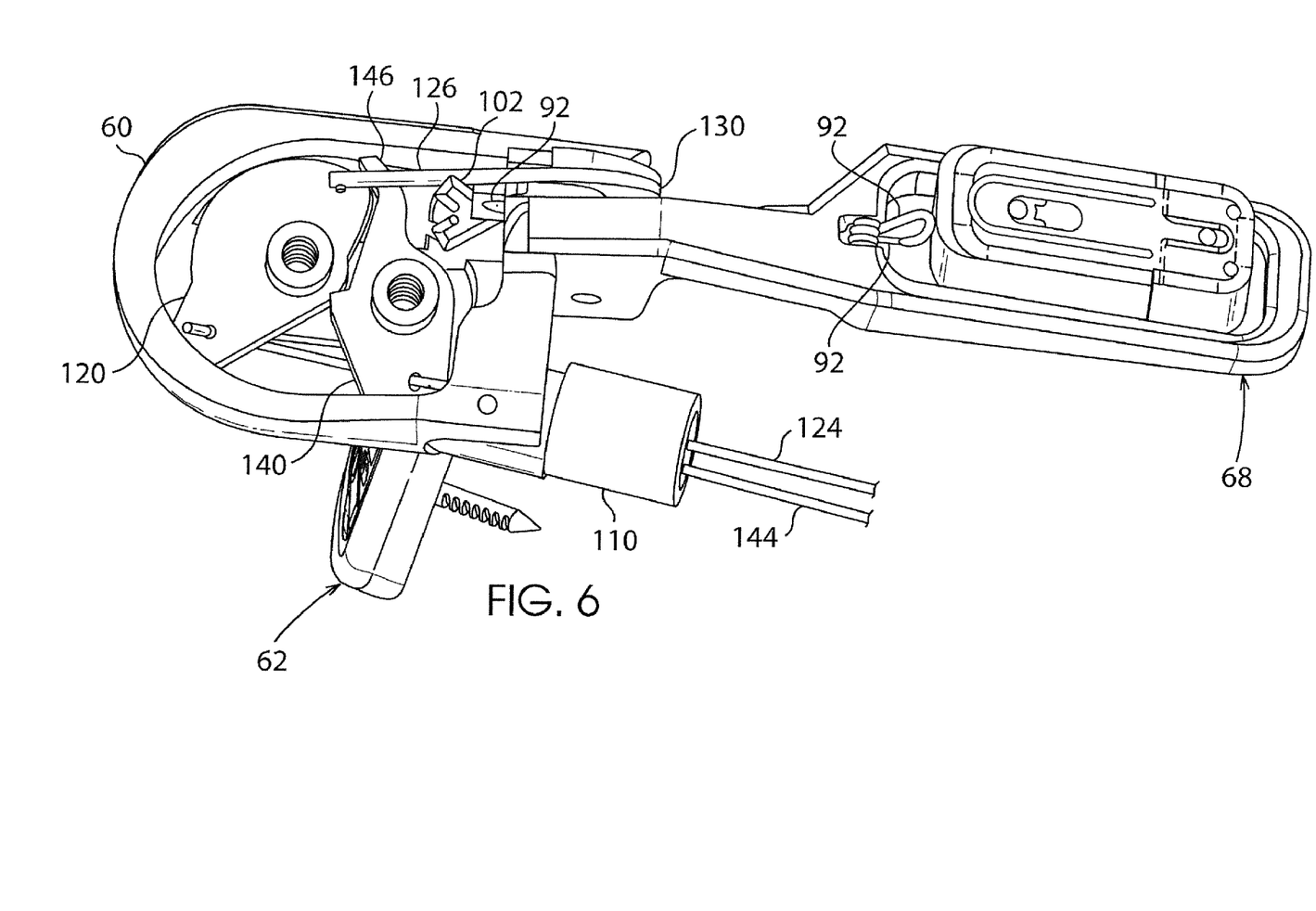
FIG. 6 is a perspective of the end effector shown without a portion of a housing while in the open position.

As shown in FIG. 6, a first bell crank 120 is rotatably mounted in the housing 60 for rotation about a screw fastener 122 (FIG. 2). A control cable 124 is connected to one side of the bell crank 120 and a wire linkage 126 is connected to the other side of the bell crank. The linkage 126 is wrapped around a hub 130 of the male jaw 62. When the control cable 124 is pushed, the bell crank 120 rotates to push the wire linkage 126 and rotate the male jaw 62 to the open position shown in FIG. 6. Pulling the control cable 124, rotates the bell crank 120 to pull the wire linkage 126 and rotate the male jaw 62 to the closed position shown in FIG. 7. Referring to FIG. 6, when the male jaw 62 is in the fully open position tissue may be positioned between the male and female jaw. As the male jaw 62 is closed, the relative position between the tissue and the female jaw 68 does not change. Thus, the configuration described above in which only the male jaw 62 rotates facilitates proper positioning of the fastener 40. Once the fastener 40 is applied and withdrawn from the receptacles of the male and female jaws, 62, 68, respectively, the control cable 124 may be pulled to rotate the bell crank 120 farther to pull the wire linkage 126 and close the jaws more as shown in FIG. 8 to facilitate withdrawal of the instrument 20 from the patient.

Figure 7:
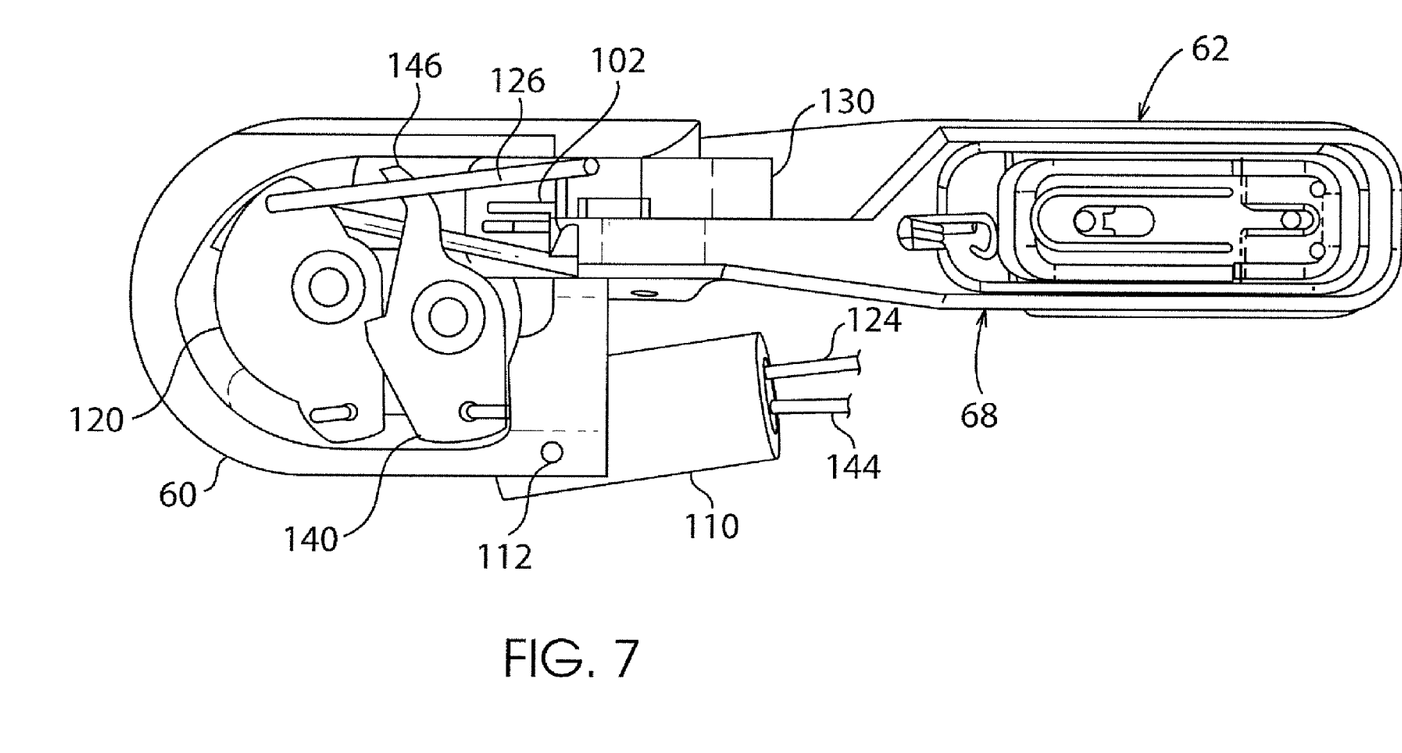
FIG. 7 is a perspective of the end effector shown without the portion of the housing while in the closed position.
Figure 8:
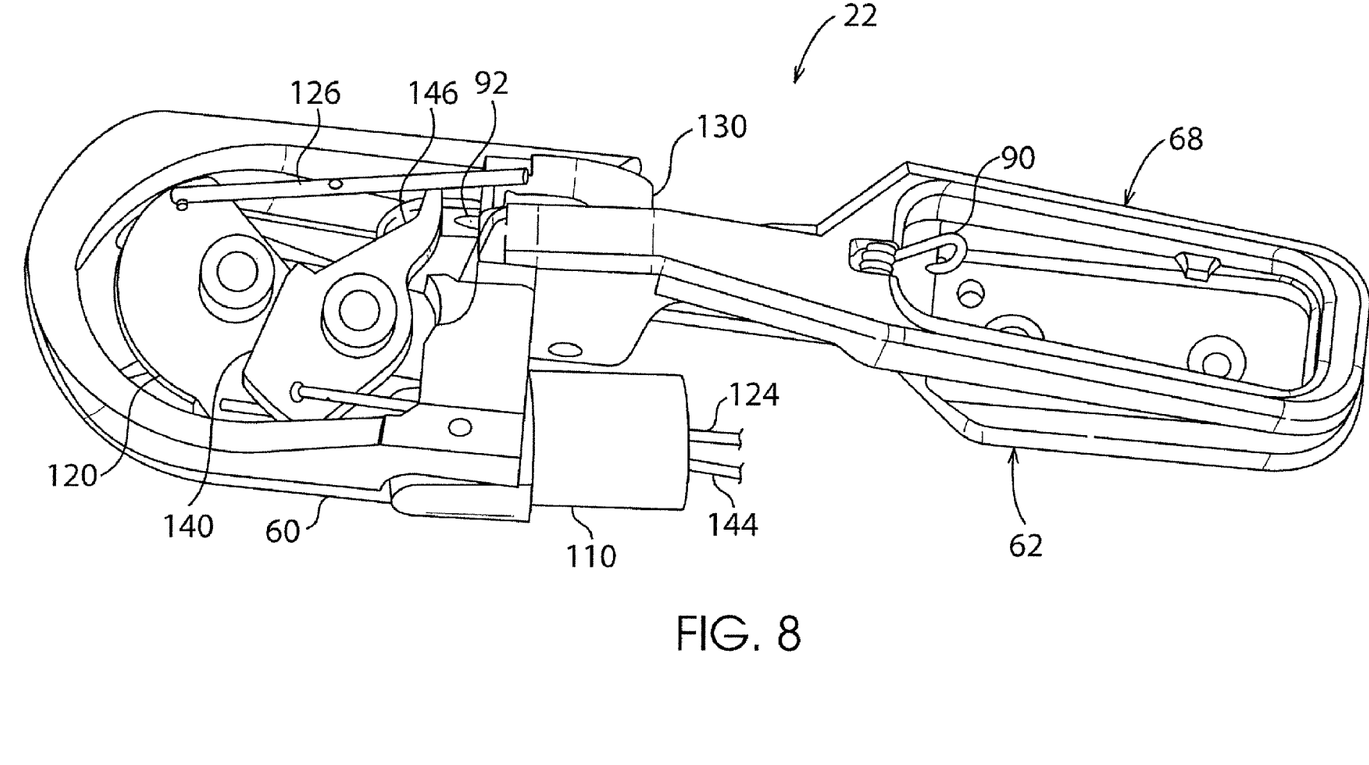
FIG. 8 is a perspective of the end effector shown without the portion of the housing while in a fully collapsed position.

Referring to FIGS. 6-8, a second bell crank 140 is also rotatably mounted in the housing 60 for rotation about another screw fastener 142 (FIG. 2). A control cable 144 is connected to one side of the bell crank 140. A finger 146 extends from the other side of the bell crank 140. The finger 146 is aligned with the push rod release element 92 and the catch 102 (FIG. 6) when the male jaw 62 is in the closed position (FIG. 7). When the male jaw 62 is in the closed position as shown in FIG. 6 and the control cable 144 is pushed, the second bell crank 140 turns forcing the finger 146 against the release element 92. As the release element 92 in the female jaw 68 moves outward in the jaw, the element engages the female component 46 to lock it on the male component 42 and to release it from the receptacle 70 of the jaw. Simultaneously, the finger 146 is forced against the catch 102 to release the stub ends 98 of the protrusions 48 from their respective counterbored holes 94, thereby releasing the male component 42 from the recess 66 of the male jaw 62. As will be appreciated by those skilled in the art, other control means may be substituted for the bell cranks 120, 140 and corresponding cables without departing from the scope of the present invention. As numerous alternative embodiments of the control means are well within the abilities of the ordinary artisan, they will not be described in any detail.

Figure 9:
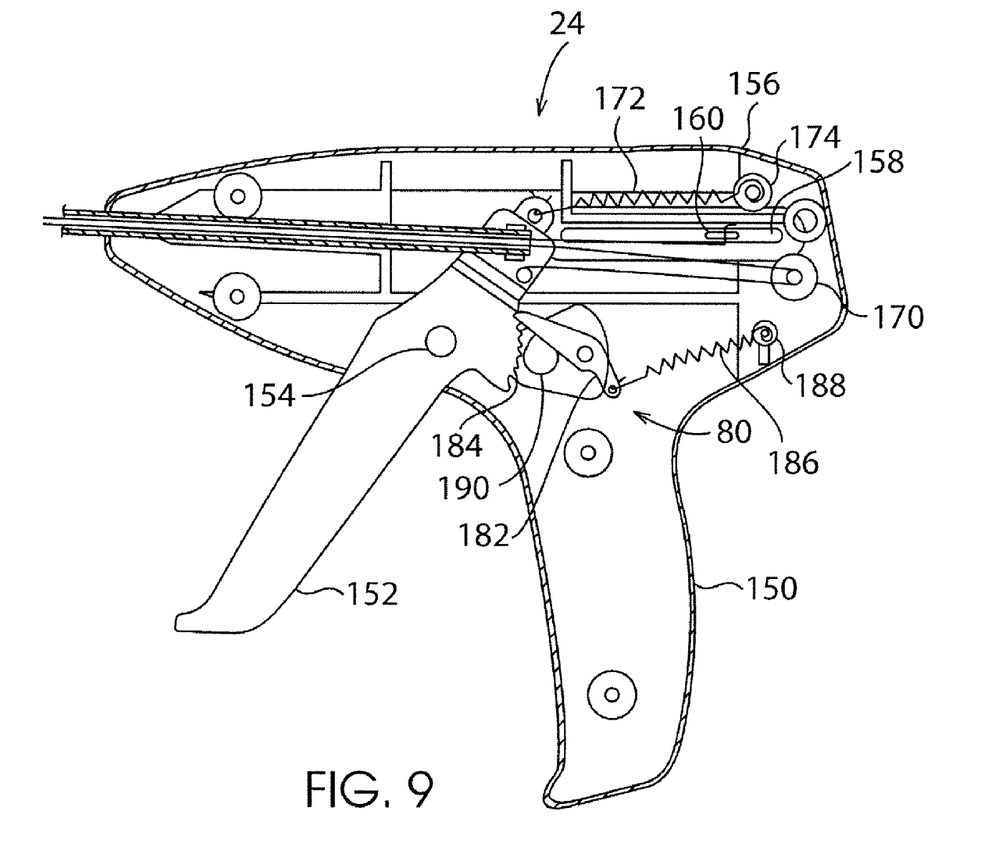
FIG. 9 is a section of a grip of the instrument.

The handle assembly 24 operates the control the male jaw 62 to open and close the end effector 22 and to lock and release the fastener 40 from the surgical instrument 20 as described in detail below. As illustrated in FIG. 9, the handle assembly 24 includes a stationary pistol grip 150 and a lever 152 pivotally attached to the grip when a pin 154. The grip 150 is integrally firmed with a housing 156 having a slot 158 forming in one side. The control cable 144 connected the second bell crank 140 controlling the push rod 92 and releasable catch 102 for locking the fastener 40 and ejecting it from the end effector 24 is attached to a sliding knob 160 captured in the slot 158. The control cable 124 extends from an end of the shaft 26, around a pulley 170 mounted in the housing and connects to the lever 152 so the control cable is pulled as the lever is moved toward the pistol grip 150 to move the male jaw 62 toward the closed position. The lever 152 is biased away from the grip 150 by a first spring 172 extending between the lever and a mount 174 on the housing 156. The lever 152 also includes a lock, generally designated by 180, for locking it in position relative to the grip 150. The lock 180 includes a pawl 182 biased against teeth 184 on the lever 152 by a spring 186 extending between the pawl and a mount 188 on the housing 156. A cam 190 mounted on the housing adjacent the pawl 182 is connected to a knob 192 (FIG. 1) that may be turned to disengage the pawl from the teeth 184 to allow the lever to return to its most forward position.

In operation, when the handle assembly lever 162 is pivoted toward to the stationary grip 150, the male jaw 62 closes. With the male jaw 62 in the closed position, the cross bar knob 160 is moved forward relative to the housing 156 to lock and release of the fastener 40. After a fastener 40 is released, the cam knob 192 is turned to release the lever lock 180 permit the lever 152 to return to its initial position and allow the male jaw 62 to open.

Although the handle assembly 24 may be made of other materials without departing from the scope of the present invention, in one embodiment the handle assembly is molded from polycarbonate. Although the end effector 22 may be made of other materials without departing from the scope of the present invention, in one embodiment the end effector is made from stainless steel.

To use the instrument 20 described above, a male component 42 of a fastener 40 is loaded in the receiver 66 of the first jaw 62 so the stub ends 98 of the protrusions 48 extend through the counterbored holes 94. The knob 160 is moved in the slot 158 so the catch 102 engages the holes 104 in the stub ends 98 of the protrusions 48 to hold the male component 42 in the receiver 66 of the first jaw. A female component 44 of the fastener 40 is loaded into the receiver 40 of the second jaw 68. The female component 44 is unlocked so its lock 54 overlaps the ledge 82 of the second jaw 68 and the lugs 84 are captured between the locking feature 86 and the head 88 to retain the female component in the receiver 40 of the second jaw.

Once the male and female components 42, 44, respectively, are loaded in the first and second jaws 62, 68, respectively, the handle assembly 150 is manipulated to position female jaw adjacent the tissue to be fastened. A conventional tissue retractor (not shown) may be used to position the tissue adjacent the female component 44 held in the female jaw 68. Once the tissue is in position relative to the second jaw 68, the lever 152 is pulled toward the handle 150 to pivot the male jaw 62 toward the tissue and the female jaw. As the male jaw 62 pivots, the protrusions 48 of the male component 42 pierce the tissue and enter the openings 52 in the female component 44. While the male jaw 62 is in this closed position, the knob 160 is moved to disengage the catch 102 from the openings 104 in the stub ends 98 of the protrusions 48 to release the male component 62. Simultaneously, the release 92 extends into the opening 80 of the female jaw 68, activating the lock 54 of the female component 44 so the protrusions 48 are locked in the openings 52. Further, the release 92 disengages the lock 54 from the ledge and spaces the locking feature 86 from the head 88 so the lugs 84 are released, thereby releasing the female component 44 from the female jaw 68. Once the male and female components 42, 44, respectively, are released from the respective jaws, the knob 192 can be turned to release the lever lock 180, allowing the lever 152 to be moved away from the grip 150. As the lever 152 is moved away from the grip 150, the jaws are spaced to completely disengage the fastener 40. The lever 152 may again be moved toward the grip 150 to totally collapse the jaws against each other as shown in FIG. 4, reducing the end effector 22 profile for withdrawing the end effector from the patient. Once removed, the end effector 22 can be reloaded and the procedure may be repeated.

Many conventional fastener systems have jaws that move relative to the handle assembly 24, making it difficult to precisely position the fastener 40 on the tissue. The instrument 20 of the present invention overcomes this problem by allowing only one jaw to move and keeping the other jaw stationary relative to the handle assembly 24.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A surgical instrument for applying a fastener to tissue of a patient, the fastener comprising a male component including a base and a protrusion, and a female component including a base and a recess for receiving the protrusion of the male component, the instrument comprising:

an elongate shaft having a working end with an end effector secured thereto and a grip end opposite the working end;

the end effector including a housing and a first jaw pivotally mounted on the housing, the first jaw including a releasable catch for releasably holding the base of the male component, the end effector also including a second jaw statically mounted to the housing, the second jaw including a releasable catch for releasably holding the base of the female component;

the first and second jaws extend from the working end of the shaft toward the grip end and the first jaw being pivotally moveable between an open position in which the first jaw is sufficiently spaced from the second jaw so that tissue can be received between a female component held in the second jaw and a male component held in the first jaw of the instrument, and a closed position in which the protrusion of the male component is aligned with and received in the recess of the female component; and a mechanism operatively connected to the first jaw for moving the first jaw between the open position and the closed position to join the male component of the fastener with the female component of the fastener thereby applying the fastener to the tissue of the patient, the mechanism including a first crank rotatably mounted in the housing coupled to a control cable extending from the first crank to the grip end and a linkage extending from the first crank to the pivotally mounted first jaw.

2. A surgical instrument as set forth in claim 1 wherein:
the protrusion of the male component is adapted to pivot relative to the base;
the first jaw includes a receiver for holding the male component; and
the receiver is adapted to maintain the protrusion substantially perpendicular to the base.

3. A surgical instrument as set forth in claim 1 wherein the second jaw includes a push rod for engaging the female component to lock the female component on the male component and to release the female component from the receiver.

4. A surgical instrument as set forth in claim 1 further comprising a handle assembly for holding and manipulating the instrument.

5. A surgical instrument as set forth in claim 4 wherein the handle assembly comprises a housing and a lever pivotally attached to the housing, the mechanism being operatively connected to the lever so that the first jaw moves between the open position and the closed position as the lever is pivoted.

6. A surgical instrument as set forth in claim 5 wherein:
handle assembly includes a grip; and
the mechanism moves the first jaw toward the closed position as the lever is pivoted toward the grip.

7. A surgical instrument as set forth in claim 1 further including a second crank rotatably mounted in the housing and coupled to a control cable extending from the second crank to the grip end.

8. A surgical instrument as set forth in claim 7, wherein the second crank includes a finger selectively controlling release of the male component from the first jaw.

9. A surgical instrument as set forth in claim 8, wherein the finger selectively engages the releasable catch of the first jaw for releasing the male component from the first jaw.

* * * * *